United States Patent [19]
Gibson et al.

[11] Patent Number: 4,931,552
[45] Date of Patent: Jun. 5, 1990

[54] PRODUCTION OF POLYOL POLYESTERS HAVING REDUCED COLOR CONTENT

[75] Inventors: Michael S. Gibson, Sacramento, Calif.; Larry N. Hawkins, Cincinnati, Ohio; Marjorie M. Peffly, Cincinnati, Ohio; Corey J. Kenneally, Maineville, Ohio; Patrick J. Corrigan, Cincinnati, Ohio

[73] Assignee: The Procter & Gamble Company, Cincinnati, Ohio

[21] Appl. No.: 364,619

[22] Filed: Jun. 14, 1989

Related U.S. Application Data

[63] Continuation-in-part of Ser. No. 213,661, Jun. 30, 1988, abandoned.

[51] Int. Cl.$^5$ .................... C07H 13/02; C07H 1/00; C11C 3/00; C09F 3/00
[52] U.S. Cl. .................... 536/119; 536/124; 260/428; 260/420; 260/410.6
[58] Field of Search .............. 536/119, 124; 260/428, 260/420, 410.6

[56] References Cited

U.S. PATENT DOCUMENTS 3,963,699  6/1976  Rizzi et al. .................. 260/234 R
3,984,444 10/1976  Ritz et al. ................... 260/405.6
4,517,360  5/1985  Volpenhein .................. 536/119
4,552,702 11/1985  Schmid et al. ............... 260/428

Primary Examiner—Ronald W. Griffin
Assistant Examiner—Pamela S. Webber
Attorney, Agent, or Firm—Robert B. Aylor; Richard C. Witte

[57] ABSTRACT

Polyol polyesters having reduced color content are prepared by base-catalyzed transesterification of lower (i.e., $C_1$–$C_3$) alkyl fatty esters having a carbonyl content of less than about 200 ppm with polyols. The esters can be prepared by a pretreatment comprising distilling the said alkyl fatty esters (in a liquid state), preferably with a base, and discarding both the top cut in an amount that is about 5% or less and at least about 2% of the still bottoms.

24 Claims, No Drawings

PRODUCTION OF POLYOL POLYESTERS HAVING REDUCED COLOR CONTENT

CROSS-REFERENCE TO RELATED APPLICATION

This is a continuation-in-part of the copending U.S. Pat. application, Ser. No. 07/213,661, filed June 30, 1988, now abandoned, of Michael S. Gibson, Larry N. Hawkins, and Marjorie M. Peffly for PRODUCTION OF POLYOL POLYESTERS HAVING REDUCED COLOR CONTENT.

TECHNICAL FIELD

This invention relates to the production of polyol fatty polyesters having reduced content of color bodies.

BACKGROUND OF THE INVENTION

The food and pharmaceutical industries have developed an interest in higher polyol polyesters of fatty acids for use as low calorie fats in food products and as pharmaceutical agents, e.g., for the lowering of blood cholesterol levels. U.S. Pat. No. 3,600,186, Mattson and Volpenhein, issued Aug. 17, 1971, describes low calorie food compositions formed by replacing at least a portion of the fat content of food products with higher polyol fatty acid polyesters. U.S. Pat. No. 3,954,976, Mattson and Volpenhein, issued May 4, 1976, describes pharmaceutical compositions for inhibiting the absorption of cholesterol comprising effective unit dosage amounts of higher polyol fatty acid polyesters, as well as the method for treating hypercholesterolemia using these polyesters. Additional pharmaceutical uses are described in U.S. Pat. No. 4,241,054, Volpenhein and Jandacek, issued Dec. 23, 1980 (removal of halogenated toxins from the body), and U.S. Pat. No. 4,264,583, Jandacek, issued Apr. 28, 1981 (treatment of gallstones). The polyol polyesters are also useful as emulsifiers.

Typical syntheses of polyol polyesters involve reaction of lower monohydric alcohol esters (e.g. methyl esters) of fatty acids with the polyol. See for example U.S. Pat. Nos. 3,963,699 Rizzi et al., issued June 15, 1976; 4,518,722, Volpenhein, issued May 21, 1985 and 4,517,360, Volpenhein, issued May 14, 1985, all incorporated by reference herein.

The fatty lower alkyl esters used in the preparation of the polyol polyesters are typically derived from natural fats and oils such as coconut oil, tallow, rapeseed oil, lard, soya oil, cottonseed oil, sunflower oil, etc. Such esters contain substantial quantities of non-carboxy carbonyl groups, as discussed hereinafter. When these esters are reacted with polyols in the presence of a basic catalyst (e.g., potassium carbonate) to produce the corresponding polyol polyesters, the resulting product is usually found to have a color, e.g., red, yellow and/or brown. Such color is undesirable, especially for situations where the polyol polyester is to be used in foods or other consumer products.

An objective of the present invention is to provide fatty polyol polyesters having reduced color content.

Another objective is to provide a process for preparing fatty polyol polyesters having reduced color content.

BACKGROUND ART

U.S. Pat. No. 3,984,444, Ritz et al., issued Oct. 5, 1976, discloses treatment of methyl esters of soya fatty acids with potassium methylate to isomerize nonconjugated double bonds in the polyunsaturated fatty chains to a conjugated form.

U.S. Pat. No. 4,552,702, Schmid et al., issued Nov. 12, 1985, discloses treatment of lower alkyl esters of fatty acids with esterification catalysts (including inter alia. alkali metal alkoxides) at temperatures above 150° C. and separating the treated esters. The treatment is said to render the esters more suitable for further processing, e.g., sulfonation.

U.S. Pat. Nos. 3,963,699 and 4,517,360, cited supra. disclose the base-catalyzed reaction of polyols with methyl esters of fatty acids to produce polyol polyesters.

SUMMARY OF THE INVENTION

Fatty polyol polyesters with good color are prepared by reacting polyols with lower alkyl esters of fatty acids having a "carbonyl content", or "carbonyl value", (These terms exclude carboxyls.) of less than about 200 ppm, preferably less than about 100 ppm, more preferably less than about 50 ppm. Low carbonyl content can be achieved if the alkyl esters are pretreated (prior to reaction with the polyol) by distillation, preferably in the presence of a strong base, e.g., an alkoxide base, that will neutralize any fatty acid that is present, removal of the initial distillate ($<5\%$, preferably $<2\%$), and leaving more than about 2%, preferably more than about 5%, more preferably more than about 6% of the initial alkyl esters in the still bottoms. These low carbonyl, e.g., pretreated, lower alkyl fatty esters, when reacted with polyols to form polyol polyesters, provide a fatty polyol polyester reaction product having minimal color.

In preferred aspects, the reaction to form polyol polyesters uses a solid polyol, especially sucrose, that is in very finely divided form; the lower alkyl fatty ester contains only a very low level of fatty acid; and/or the reaction uses only very low levels of catalyst.

DETAILED DESCRIPTION OF THE INVENTION

One aspect of the present invention involves the use of lower (i.e., $C_1$–$C_3$) alkyl esters of $C_6$–$C_{22}$ fatty acids that have a low content of carbonyl groups such as aldehyde and/or ketone groups and/or groups that are precursors of such groups, e.g., peroxy groups. These low carbonyl content esters can be prepared by a process which comprises distilling said lower alkyl esters of fatty acids in a liquid state, preferably with from about 0.01% to about 5%, preferably less than about 1%, of a compatible base, at a temperature of from about 100° C. to about 300° C. and removing about 5%, or less, preferably about 2%, or less, of the initial distillate ("light cut", or "top cut"). The initial distillate contains a very high content of compounds that contain carbonyl groups. If the source lower alkyl esters are already low in carbonyl content, then a lesser amount of the top cut can be discarded. However, if the source lower alkyl esters have a relatively high content of carbonyl groups, then more of the top cut should be discarded. Similarly, the carbonyl content of the source lower alkyl esters determines how much should be left in the still bottoms. In general, the higher the initial content of carbonyl groups, the greater the amounts of both top cut and still bottoms must be discarded to achieve the desired level of carbonyl content in the distilled lower alkyl esters and thus the desired low level of color in the finished polyol polyester.

If the source lower alkyl esters have too high a carbonyl content, then it is desirable to have a strong base present during distillation.

This distillation process results in methyl esters with carbonyl contents [other than the carbonyls associated with carboxy groups

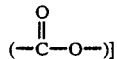

that are typically less by about 100–400 ppm than the original contents. Carbonyl contents below about 200 ppm, preferably less than about 100 ppm, more preferably less than about 50 ppm, are especially desired.

The invention relates to the preparation of polyol polyesters by reacting a polyol with lower alkyl fatty esters which have a low level of carbonyl content, e.g., esters that have been treated according to the above-described treatment process, in the presence of a basic catalyst, with concurrent removal from the reaction mix of the lower (i.e., $C_1$–$C_3$) alcohol which is formed during the reaction. This results in the production of polyol polyesters having color content which is substantially less than that of polyol polyesters which are prepared from lower alkyl fatty esters which have higher carbonyl contents.

The preparation of the polyol polyesters from the treated lower alkyl fatty esters can be accomplished by a known procedure of reacting the lower alkyl fatty esters with polyol in the presence of basic catalyst such as alkali metal alkoxides, hydroxides, hydrides and carbonates. See, for example, U.S. Pat. Nos. 3,963,699, Rizzi et al., issued June 15, 1976; 2,893,990, Hass et al., issued July 7, 1959; 4,518,722, Volpenhein, cited supra: and 4,517,360, Volpenhein, cited supra; all incorporated by reference herein.

As used herein, the term "polyol" is intended to include any aliphatic or aromatic hydroxy compound containing at least two free hydroxyl groups. The selection of a suitable polyol is simply a matter of choice. For example, suitable polyols can be selected from the following classes: saturated and unsaturated straight and branched chain linear aliphatics; saturated and unsaturated cyclic aliphatics, including heterocyclic aliphatics; or mononuclear or polynuclear aromatics, including heterocyclic aromatics. Carbohydrates (e.g., monosaccharides) and nontoxic glycols are preferred polyols. Monosaccharides suitable for use herein include, for example, glucose, mannose, galactose, arabinose, xylose, ribose, apiose, rhamnose, psicose, fructose, sorbose, tagitose, ribulose, xylulose and erythrulose. Oligosaccharides suitable for use herein include, for example, maltose, kojibiose, nigerose, cellobiose, lactose, melibiose, gentiobiose, turanose, rutinose, trehalose, sucrose and raffinose. Polysaccharides suitable for use herein include, for example, amylose, glycogen, cellulose, chitin, inulin, agarose, zylans, mannan and galactans. Although sugar alcohols are not carbohydrates in a strict sense, the naturally occurring sugar alcohols are so closely related to the carbohydrates that they are also included as preferred materials for use herein. The sugar alcohols most widely distributed in nature and preferred for use herein are sorbitol, mannitol and galactitol.

Particularly preferred classes of materials suitable for use herein include the monosaccharides, the disaccharides and sugar alcohols. Preferred carbohydrates and sugar alcohols include xylitol, sorbitol and sucrose.

The preferred polyol is sucrose. Sucrose is a solid and should be in a very finely divided form. Processes for achieving finely divided sucrose are disclosed in U.S. Pat. Nos.: 3,644,333 and 3,792,041, said patents being incorporated herein by reference. In addition, one can reduce, e.g., by mechanical processes, the particle size of the sucrose and/or remove larger particles to the desired particle size, i.e., all particles are less than about 50 microns, preferably less than about 30 microns, more preferably less than about 10 microns.

As used herein, the term "lower alkyl fatty esters" refers to the $C_1$–$C_3$ alkyl esters of fatty acids containing from 6 to 22 carbon atoms in the fatty acid chain. The fatty acids typically are those which contain an appreciable content of unsaturation and these are the ones that are most likely to have higher carbonyl contents. Unsaturated fatty acids, and especially those with carbonyl contents above about 400 ppm, receive the largest benefit from the pretreatment. It is highly desirable to minimize contact of air with the esters to avoid creation of the carbonyl compounds and/or peroxide compounds that are the precursors of the carbonyl compounds.

The lower alkyl fatty esters herein are derived from natural fats and oils in which the fatty acid moieties comprise those having chain lengths of 6 to 22 carbon atoms. Some of said fatty acid moieties can be, and usually are, unsaturated and even contain multiple sites of unsaturation which are either conjugated or conjugatable. The fatty acids from these oils are typically mixtures of saturated and unsaturated acids of various chain lengths. For example, methyl esters made from soybean oil will contain, inter alia, methyl palmitate, methyl stearate, methyl oleate, methyl linoleate and methyl linolenate. The lower alkyl fatty esters are typically prepared by alcoholysis of fats and oils or by hydrolysis of fats and oils followed by reaction of a lower alcohol with the free fatty acids produced by the hydrolysis. Examples of fats and oils from which the fatty acids are derived are tallow, lard, soybean oil, sunflower oil, safflower oil, coconut oil, and corn oil. Specific fatty acids from fats and oils are octanoic, decanoic, lauric, myristic, palmitic, stearic, behenic, erucic, elaidic, linoleic, linolenic, eleostearic, arachidonic and parinaric acids. Typically the oils will be at least partially hydrogenated prior to their conversion to lower alkyl fatty esters.

While the present invention is not to be limited to any theory, the distillation process reduces the carbonyl content of the methyl esters and low carbonyl content in the lower alkyl ester correlates with reduced color of the polyol polyester. Since the carbonyl content can increase in the presence of oxygen, it is desirable to minimize the subsequent atmospheric oxidation. This can be done by promptly cooling the methyl esters after distillation and/or storing the methyl esters and/or polyol polyester under conditions that reduce exposure to oxygen, e.g., in a closed container, preferably under nitrogen. Use of lower alkyl fatty esters having low carbonyl content in accordance with the present invention, results in less color bodies (and/or their precursors) in the resulting polyol polyesters.

As discussed hereinbefore, very small quantities of color bodies can result in undesirable color in the finished polyol polyesters. The present invention can minimize the post-treatment, e.g., bleaching, of the resulting polyol polyesters that is required to reach a given color target.

All percentages and ratios herein are "by weight" unless specified otherwise.

The pretreatment process for the lower alkyl fatty esters is typically as follows.

The lower alkyl fatty esters initially are in a liquid state, and usually contain a base, typically a strong base, even an alkoxide or a hydride, of an alkali or alkaline earth metal or aluminum. The base usually is already present from the reaction used to form the esters. However, it can be added in the form of a dry powder or, for alkoxides, an alcoholic solution containing from about 5% to about 30% alkoxide base. The amount of base present, if any, is preferably very low. For example, the preferred level is from about 0.01% to about 0.5%, preferably from about 0.02% to about 0.25% based on the fatty acid ester. The amount of base is preferably at least enough to neutralize any free fatty acid since free fatty acid interacts with the catalyst used to prepare the polyester. Levels above about 1%, based on the ester, can generate excessive amounts of soap. Excessive soap leads to excessive foaming and/or formation of undesirable phases. These problems can be overcome by removing the undesirable products by filtration, centrifugation, etc., and/or addition of defoamants to overcome the foaming problems. Amounts of base that are typically present provide a weight ratio of base to ester of at least about 0.0001:1, preferably from about 0.001 to about 0.005:1, and most preferably about 0.0025:1. The esters are then distilled. The conditions of distillation are within the range of from about 100° C. to about 300° C., preferably from about 175° C. to about 260° C., more preferably from about 200° C., to about 250° C. and at a pressure that will permit distillation to occur, typically from about 1 to about 50 mm Hg. The specific distillation conditions chosen for a particular lower alkyl fatty ester product will depend upon the boiling characteristics of that ester product. The light cut and, desirably, the still bottoms are separated and the remaining distilled esters (distillate) usually are clear and water white.

The portion of the ester feed stock that remains after distillation (still bottoms) is typically from about 2% to about 20%, more typically from about 6% to about 12%, and contains a large amount of non-carboxy carbonyl groups. The amount of still bottoms is determined by the feed stock. E.g., if it is a crude feed stock, there will be more and if the feed stock has been previously treated (especially distilled), it will normally be less. Fractional distillation is preferred.

As discussed hereinbefore, the distillation separates the desired esters from both a low molecular and/or more volatile portion and a higher molecular weight portion, both of which are higher in non-carboxy carbonyl groups. Typically, the initial distillate will contain from about 0.5% to less than about 5% by weight of the total esters, more preferably from about 1% to about 4%, most preferably about 2% or less, by weight of the total fatty acid esters. This "top cut" can also contain other extraneous materials such as free alcohol and/or glycerine. Also, typically, the high molecular weight fraction (still bottoms) contains at least about 2%, and preferably at least about 5% of the total fatty acid esters.

A reduction in non-carboxy carbonyl content can be achieved in any distillation of fatty acid esters of short chain alcohols by separating the first portion of the fatty acid esters which is distilled, as compared to a distillation in which no top cut is taken. A further reduction can be achieved by removing the still bottoms. A normal distillation without removal of a top cut or still bottoms can actually raise the carbonyl level.

As discussed hereinbefore, it is desirable to keep the level of free fatty acid in the lower alkyl fatty ester to a minimum. The fatty acids interact with the catalyst that is used in the polyol polyester reaction and interfere with the reaction. It is therefore desirable to avoid bringing the low carbonyl lower fatty alkyl esters into contact with water, especially under conditions which would promote the formation of fatty acids. The level of free fatty acid in the lower alkyl fatty esters is preferably less than about 0.1%, more preferably less than about 0.05%, and even more preferably less than about 0.01%.

The very strong bases which can be used in the pretreatment of the lower alkyl fatty esters in the present invention can have the formula $M(L)_n$, wherein L is H, (RO), borohydride, or mixtures thereof, wherein R is an alkyl radical of from 1 to about 5 carbon atoms, M is an alkali metal (i.e., a metal from Group IA of the Periodic Table of Elements), an alkaline earth metal (i.e., a metal from Group IIA of the Periodic Table of Elements) or aluminum, and n is 1 when M is alkali metal, 2 when M is alkaline earth metal, and 3 when M is aluminum. The term "alkyl" in describing the alkoxide bases includes unsubstituted alkyl and substituted alkyl radicals such as, for example, benzyl, haloalkyl, nitroalkyl, and the like. Preferred bases are those wherein R contains from 1 to 4 carbon atoms. Examples of bases for use in the present invention are: sodium and potassium hydride, calcium hydride, lithium aluminum hydride, sodium borohydride, sodium methoxide, potassium methoxide, sodium ethoxide, sodium 2-chloroethoxide, lithium ethoxide, sodium propoxide, potassium propoxide, sodium isopropoxide, sodium butoxide, calcium diethoxide, magnesium diisopropoxide, barium dibutoxide, aluminum triisopropoxide and aluminum tritertiarybutoxide. As is known in the art, these bases in which M is an alkali metal are made by reacting the corresponding alcohol (e.g., ethanol to make the ethoxide) or hydrogen with the alkali metal. The alkoxides can also be formed by reacting the desired alcohol with the alkali metal hydride. Alkoxide bases in which M is aluminum are made, e.g., by reacting aluminum chloride with the alkali metal alkoxide of the corresponding alcohol (e.g., reacting one mole of aluminum chloride with three moles of sodium isopropoxide to make one mole of aluminum triisopropoxide.

The preferred very strong bases for pretreatment of the lower alkyl fatty esters are the alkali metal alkoxides, e.g., sodium and potassium alkoxides, especially the sodium and potassium methoxides and ethoxides. Solutions of the alkoxides are preferred for the distillation.

In the preparation of polyol polyesters of improved color (i.e., having reduced color content) the lower alkyl fatty esters with low carbonyl content such as those that have been pretreated as described above are reacted with polyol in the presence of a basic catalyst in accordance with known procedures. See for example U.S. Pat. No. 2,893,990, Hass et al., issued July 7, 1959. One procedure is that described in U.S. Pat. No. 4,517,360, Volpenhein, cited supra. and incorporated by reference herein. According to this process, a molten mixture is formed containing the lower alkyl fatty ester, polyol, an alkali metal fatty acid soap, and basic catalyst which can be selected from sodium carbonate, potassium hydroxide, potassium carbonate, barium carbonate, any of the other known catalysts, or mixtures thereof. The reaction mixture can contain from about 5% to about 50% polyol, from about 10% to about 90% lower alkyl fatty ester, from about 1% to about 30% of soap, and from about 0.01% to about 5% of basic catalyst. It is a special advantage of the low carbonyl content of the lower alkyl fatty esters that the level of catalyst can be reduced to less than about 0.1, preferably to less than about 0.05, more preferably to less than about 0.01, molar equivalents of catalyst per mole of polyol. This low level of catalyst results in improved color as compared to conventional catalyst levels. The lower the levels of carbonyl values and/or fatty acids that are present, the lower the level of catalyst can be.

Typically, the molar ratio of soap:polyol is from about 0.75:1 to about 1:1. Excess lower alkyl fatty ester can then be added to this melt, the amount being sufficient to raise the overall ester:polyol mole ratio above the amount required for total esterification (8:1 for sucroses), and the mixture is reacted at a temperature of from about 100° C. to about 160° C. and pressure of from about 0.1 to about 60 mm Hg for from about 1 to about 20 hours. The fatty polyol polyesters can then be separated from the reaction mix by conventional means such as solvent extraction, water washing, etc.

The present invention will be illustrated by the following examples.

EXAMPLE I

The oil (triglyceride) derived by the partial hydrogenation of refined soybean oil is converted to the methyl ester by methanolysis in the presence of 0.25% sodium methoxide (sodium methylate) and distilled. The Carbonyl Value (CV) of the starting crude ester is approximately 400 ppm. The distillation temperature is about 218° C. and a top cut is separated containing about 2% of the methyl ester. The distilled crude methyl ester is clear and nearly water white. The near water white methyl ester has a non-carboxy carbonyl value of about 46 ppm.

A portion of the crude methyl ester is distilled with a 2% top cut without any significant levels of sodium methoxide present. This portion of the ester has a carbonyl content of about 326 ppm.

A sample of the methyl ester distilled with the sodium methoxide in accordance with the present invention and a sample from the portion which is not distilled with sodium methoxide are both converted to sucrose polyester according to the procedure of U.S. Pat. 4,517,360, cited supra.

6.3 gm of potassium hydroxide (85% KOH) is dissolved in 25 gm methanol, and allowed to stir on a magnetic stirrer.

254 gm of methyl ester is added to a three-neck flask fitted with a mechanical agitator, thermometer, reflux condenser, and heating mantle. Slow agitation is started and the methanolic potassium hydroxide solution is added to the stirring methyl esters. The mixture is heated under a nitrogen blanket to reflux and held there for 20 minutes.

The reflux condenser is then converted to allow distillation of methanol that will occur in the next step.

51 gm of sucrose and 2.1 gm of potassium carbonate are added to the stirring mixture. Heating is continued allowing the slow distillation of methanol from the mixture. When the methanol is removed the temperature is allowed to rise to 100° C.

Full vacuum is slowly applied (1–5 mm Hg) and the temperature is raised to 135° C. Temperature is held at 135° C. for 1.5 hours until the sucrose is partially esterified and drawn into solution.

Pressure is brought to atmospheric with nitrogen and an additional 309 gm of methyl ester is added to the mixture.

Full vacuum (1–5 mm Hg) is applied slowly, and the reaction is continued at full vacuum and about 135° C. for four hours.

The reaction is then cooled to below 100° C. and 25 ml of distilled water is added to hydrate the potassium soap formed in the mixture. The soap sludge is then removed by centrifugation.

The sucrose polyester (SPE) oil produced in the reaction is then washed three times with water at approximately 60° C. and the washed oil then dried on a Rotovap ®.

The oil is bleached at approximately 60° C. with 17 gm of bleaching earth and is then filtered.

Excess methyl ester is removed by thin film evaporation at high vacuum, and the product deodorized by steam distillation.

TABLE 1

| Ester Treatment | Methyl Ester CV (PPM) | SPE Lovibond Red Color |
|---|---|---|
| None | 400 | 5.0 |
| Distillation with 0.25% Na Methoxide; 2% top cut | 46 | 1.1 |
| Distillation w/o Na Methoxide; 2% top cut | 326 | 5.6 |

As can be seen from the above, the process of the invention gives methyl esters with a very low CV and the resulting SPE has minimal color. The distillation without a base and a 2% top cut reduces the CV, but in this example the CV reduction was insufficient to guarantee an improvement in SPE color. If the methyl ester has a lower starting CV, and/or sufficient still bottoms, then a distillation without base and a 2% top cut will have a sufficiently low CV.

PREPARATIVE EXAMPLE II

A highly oxidized, distilled methyl ester of soybean fatty acids having a carbonyl value of about 520 ppm is redistilled with about 0.2% added sodium methylate. The ester is split into three equal parts and distilled under different conditions as follows:

(1) Vacuum - 40 mm Hg; 260° C.; 2.2% top cut; 8.2% still bottoms; and 89.6% distillate.
(2) Vacuum - 20 mm Hg; 250° C.; 2.0% top cut; 4.9% still bottoms; and 93.1% distillate.
(3) Vacuum - 5 mm Hg; 230° C.; 2.1% top cut; 4.5% still bottoms; and 93.4% distillate.

The carbonyl values for the products are about as follows: (1) 140 ppm; (2) 240 ppm; and (3) 340 ppm. There is a substantial amount of carbonyl content in both the high boiling fraction and in the low boiling fraction in the range of 3,500–6,000 ppm. This example shows that as a higher percentage of still bottoms is removed, the carbonyl value of the distillate is reduced.

PREPARATIVE EXAMPLE III

A methyl ester is prepared from soybean oil using sodium methylate as the transesterification catalyst. The esters are water washed to remove all traces of the catalyst. Titration with a strong acid reveals no strong base and no soaps present. The carbonyl value of this ester is about 230 ppm, indicating that the esters are not highly oxidized. This ester is distilled at about 215° C. under a vacuum of about 5 mm Hg to give an approximately 2.4% top cut, about 9.6% still bottoms, and about 87.5% distillate having a carbonyl value of about 40 ppm.

When the above process is repeated but the water washing step is eliminated, approximately 0.02% sodium methylate remains in the crude ester. A crude ester of this type with a carbonyl value of about 190 ppm is distilled as 219° C., 5 mm Hg vacuum, 2.2% top cut, 11.1% still bottoms, and 85.4% distillate. The carbonyl value of the final distillate is about 20 ppm.

The above results indicate that the strong base is not required for low carbonyl values. However, the strong base, when used at significant levels, can help reduce the carbonyl value of the distillate. The strong base is also helpful in avoiding the formation of free fatty acids during distillation.

EXAMPLE IV

Soybean methyl esters having both high and low carbonyl values are blended together to give methyl esters with carbonyl values of 86 ppm, 148 ppm, and 351 ppm, respectively. These methyl esters are then used to make sucrose octaesters having about 84%, 93% and 88% content of octaesters, respectively, using a process similar to that in Example I. The sucrose octaesters are filtered through 1.76%, 1.85%, and 2.0% Filtrol bleach respectively. The Lovibond Red values for the three products were 0.9, 1.1, and 2.1, respectively. These data indicate that the color of the finished polyol polyester is directly related to the carbonyl values of the lower alkyl esters used to make the polyol polyesters.

EXAMPLE V

The reaction apparatus is a 1-liter glass reactor with a heating mantle, agitator, thermometer, thermowatch, and methanol condenser. Vacuum is applied to the reactor through the methanol condenser.

In this set of experiments, about 25 gm of sucrose and the desired amount of potassium carbonate are dissolved in water. About 25 gm of potassium stearate soap and about 320 gm of partially hydrogenated soybean methyl esters are added to the water solution. This mixture is agitated and heated to about 60° C. under vacuum until almost all of the water is evaporated. This step gives sucrose with a particle size less than about 10 microns. The reactor is then heated to about 135° C., under vacuum, to start the reaction. The mixture is reacted at this temperature for about 5.5 hours, or until greater than 95% of the sucrose esters in the mixture are sucrose octaesters.

The reaction is terminated by breaking the vacuum with nitrogen, and cooling the reaction mixture to ambient temperature. The reaction mixture is then hydrated with a small amount of water (about 6% by weight) and centrifuged to remove the soap. The mixture is bleached with about 1% Filtrol bleach for about 10 minutes at about 60° C. The red and yellow colors of this refined mixture are measured on a Lovibond Tintometer.

Three levels of potassium carbonate catalyst, and two different types of esters are used in this study. The two esters are both soybean esters, and differ only by their carbonyl values, as shown below.

TABLE 2

| Ester | Carbonyl Value | Free Fatty Acid |
|---|---|---|
| #1 | 70 ppm | None detected |
| #2 | 40 ppm | None detected |

The analyses for the refined products from the esterification reactions of these esters are shown below.

TABLE 3

| Ester | Amount of Carbonate | Reaction Time (hrs.) | Percent Octaester | Lovibond Red | Lovibond Yellow |
|---|---|---|---|---|---|
| #1 | 1.4 gm | 5.5 | 87.5 | 4.0 | 29 |
| #1 | 0.25 gm | 5.5 | 97.9 | 2.8 | 17 |
| #1 | — | 5.5 | 74.9 | 1.8 | 11 |
| #2 | — | 4.5 | 98.5 | 0.3 | 1.3 |

The conclusions from this data are that lower levels of catalyst give a better reaction and a better color product. However, as the carbonyl value of the ester increases, a certain minimum amount of catalyst is necessary to overcome the poisoning effects of the carbonyl compounds in the ester. The reactions using no added potassium carbonate are apparently being catalyzed by the small amount of residual strong base in the soap. This residual strong base is measured to be about 0.23% by weight of the soap. This amounts to approximately 0.06 gm of strong base. This is about 0.014 mole per mole of polyol.

EXAMPLE VI

This example demonstrates the effect of free fatty acid in the fatty esters on the esterification reaction with sucrose. The reaction apparatus is the same as in Example V.

In this set of experiments, the reaction is carried out in two stages. In the first stage, about 148 gm of soybean methyl esters, about 34 gm of sucrose, about 25 gm of potassium stearate soap, and about 1.4 gm of potassium carbonate are added to the reactor. Vacuum is applied to the reactor, the reactor is heated to about 135° C., and the reaction is continued for about 1.5 hours. At the end of about 1.5 hours, the vacuum is broken with nitrogen, and about 207 gm of soybean methyl esters and about 1.4 gm of potassium carbonate are added to the reactor. Vacuum is reapplied to the reaction, the contents are reheated to about 135° C., and the second stage of the reaction is continued for about 4 hours. At the end of the second stage (about 5.5 hours total reaction time), the contents are cooled to ambient temperature, and are sampled and analyzed for octaester conversion.

This reaction procedure is used in a series of experiments where soybean methyl esters with differing levels of free fatty acid are tested. The free fatty acid content is determined as stearic acid. The table below shows the octaester conversion after a total reaction time of about 5.5 hours. The term "octaester conversion" refers to the percentage of all the sucrose esters in the reaction mix that are octaesters.

TABLE 4

| % Fatty Acid in the Esters | Octaester Conversion after about 5.5 hours |
| --- | --- |
| None detected | 91% |
| 0.05% | 71% |
| 0.1% | 39% |
| 0.2% | 0% |

What is claimed is:

1. A process for preparing polyol polyesters of improved color from polyols and $C_1$-$C_3$ alkyl esters of $C_6$-$C_{22}$ fatty acids comprising said reacting $C_1$-$C_3$ alkyl fatty esters having a carbonyl content of less than about 200 ppm with a polyol in the presence of a catalyst for the reaction and concurrently removing from the reaction mix the $C_1$-$C_3$ alcohol formed during the reaction.

2. The process of claim 1 wherein the carbonyl content of said fatty esters is less than about 100 ppm.

3. The process of claim 1 wherein the carbonyl content of said fatty esters is less than about 50 ppm.

4. The process of claim 1 wherein said fatty esters are given a pretreatment comprising distilling said $C_1$-$C_3$ alkyl fatty acid esters in a liquid state with up to about 5% of a base and separating the first distillate containing from about 0.5% to about 5% of said fatty esters and the still bottoms containing at least about 2% of said alkyl fatty esters from the product.

5. The process of claim 4 wherein said base is about as strongly basic as an alkoxide having the formula $(RO)_nM$, wherein R is an alkyl radical of from 1 to about 5 carbon atoms, M is an alkali metal, an alkaline earth metal or aluminum, and n is 1 when M is alkali metal, 2 when M is alkaline earth metal, and 3 when M is aluminum, said base being present at a level of from about 0.01% to about 5%.

6. The process of claim 5 wherein said base has the formula $M(L)n$ wherein L is selected from the group consisting of H, (RO), borohydride, and mixtures thereof, wherein R is an alkyl radical of from 1 to 5 carbon atoms, M is selected from the group consisting of alkali metals, alkaline earth metals, aluminum, and mixtures thereof, and n is 1 when M is alkali metal, 2 when M is alkaline earth metal, and 3 when M is aluminum.

7. The process of claim 6 wherein said base is selected from the group consisting of said alkoxide, the corresponding hydrides of said M metals, alkali metal borohydrides, and mixtures thereof.

8. The process of claim 7 wherein said base is an alkoxide and M in the alkoxide is an alkali metal.

9. The process of claim 4 wherein the distillation is at a temperature of from about 100° C. to about 300° C.

10. The process of claim 9 wherein the esters are methyl esters and said temperature is from about 175° C. to about 260° C.

11. The process of claim 4 wherein the first distillate containing less than about 2% of said alkyl fatty esters and still bottoms representing at least about 6% of said alkyl fatty esters are separated from the product.

12. The process of claim 11 wherein the alkyl fatty esters are methyl esters.

13. The process of claim 12 wherein the M in the alkoxide base is an alkali metal.

14. The process of claim 1 wherein said polyol is selected from the group consisting of monosaccharides, disaccharides and sugar alcohols.

15. The process of claim 14 wherein said process comprises:
   i. forming a molten mixture comprising the said $C_1$-$C_3$ alkyl fatty acid ester, an alkali metal fatty acid soap and a basic catalyst;
   ii. reacting the mixture from (i.) at from about 100° C. to about 160° C. and a pressure of 0.1 to about 10 mm Hg;
   iii. adding any additional $C_1$-$C_3$ alkyl fatty ester to the melt of (i.) needed to give a final overall ester:-polyol mole ratio of the reactants to provide at least about 95% esterification of said polyol; and
   iv. separating the resultant polyol polyester from the reaction mix.

16. The process of claim 15 wherein said polyol is sucrose.

17. The process of claim 16 wherein said alkyl fatty esters contain less than about 0.1% fatty acid.

18. The process of claim 17 wherein said alkyl fatty esters contain less than about 0.05% fatty acid.

19. The process of claim 18 wherein said alkyl fatty esters contain less than about 0.01% fatty acid.

20. The process of claim 19 wherein said catalyst is used at a level of less than about 0.05 mole per mole of said polyol and the carbonyl content of said alkyl fatty esters is less than about 50 ppm.

21. The process of claim 20 wherein said catalyst is used at a level of less than about 0.01 mole per mole of polyol.

22. The process of claim 18 wherein said catalyst is used at a level of less than about 0.1 mole per mole of polyol and the carbonyl content of said alkyl fatty esters is less than about 100 ppm.

23. The polyol polyesters prepared by the process of claim 1.

24. The sucrose octaesters prepared by the process of claim 22.

* * * * *

UNITED STATES PATENT AND TRADEMARK OFFICE
CERTIFICATE OF CORRECTION

PATENT NO. : 4,931,552

DATED : June 5, 1990

INVENTOR(S) : M. S. Gibson, L. N. Hawkins, M. M. Peffly, C. J. Kenneally and P. J. Corrigan It is certified that error appears in the above-identified patent and that said Letters Patent is hereby corrected as shown below:

Col. 11, line 13, "said reacting" should read -- reacting said --.

Signed and Sealed this

Seventeenth Day of March, 1992

Attest:

HARRY F. MANBECK, JR.

*Attesting Officer*　　　　　*Commissioner of Patents and Trademarks*